United States Patent [19]
Kajiwara et al.

[11] Patent Number: 5,379,765
[45] Date of Patent: Jan. 10, 1995

[54] MONITORING APPARATUS FOR USE IN OBTAINING BRONCHIAL ELECTROCARDIOGRAM

[76] Inventors: Nagao Kajiwara, 3-21, Aoki 1-chome, Kawaguchi-shi, Saitama-ken; Takayoshi Watanabe, 6-6-301, Sarugaku-cho 1-chome, Chiyoda-ku, Tokyo, both of Japan

[21] Appl. No.: 986,039

[22] Filed: Dec. 4, 1992

[30] Foreign Application Priority Data

Jun. 12, 1991 [JP] Japan .................. 3-360403

[51] Int. Cl.⁶ .......................................... A61B 5/0402
[52] U.S. Cl. .................... 128/642; 607/122
[58] Field of Search ............ 128/639, 642, 783–784, 128/786; 607/116, 122, 124, 133

[56] References Cited

U.S. PATENT DOCUMENTS

| | | | |
|---|---|---|---|
| 4,304,239 | 12/1981 | Perlin | 128/642 |
| 4,351,330 | 9/1982 | Scarberry | 607/124 X |
| 4,383,534 | 5/1983 | Peters | |
| 4,649,924 | 3/1987 | Taccardi | 128/642 |
| 5,025,786 | 6/1991 | Siegel | 128/642 |
| 5,056,532 | 10/1991 | Hull et al. | 607/124 |
| 5,069,215 | 12/1991 | Jadvar et al. | 607/124 X |
| 5,125,406 | 6/1992 | Goldstone et al. | 128/642 |

FOREIGN PATENT DOCUMENTS 0428863 7/1991 European Pat. Off. .

*Primary Examiner*—Angela D. Sykes
*Attorney, Agent, or Firm*—Wenderoth, Lind & Ponack

[57] ABSTRACT

An intrabronchial catheter has an inflatable balloon on which the bronchial ECG lead electrodes are mounted. Upon inserting the intrabronchial catheter into the trachea or bronchus of a human body, air is supplied to the balloon so that the balloon is stably retained in the trachea or bronchus, thereby bringing the bronchial ECG lead electrodes in close contact with the internal wall surface of the trachea or bronchus so as to effectively obtain a bronchial electrocardiogram or effect cardiac pacing.

12 Claims, 7 Drawing Sheets

MONITORING APPARATUS FOR USE IN OBTAINING BRONCHIAL ELECTROCARDIOGRAM

BACKGROUND OF THE INVENTION

1. Field of the Invention

This invention relates generally to an apparatus for conducting a bronchial electrocardiogram, and more particularly to an intrabronchial catheter of a bronchial electrocardiographic apparatus, which is inserted into the trachea or bronchus of a human body and is provided at the leading end portion thereof with a balloon having electrocardiographic lead electrodes, capable of being inflated within the trachea or bronchus of the human body so as to bring the lead electrodes internal close contact with the internal surface of the trachea or bronchus.

2. Description of the Prior Art

An electrocardiogram is essential to diagnose possible heart disorders such as arrhythmia and ischemia. Body-surface electrocardiography which is the most popular electrocardiography practiced at present, transesophageal lead electrocardiography capable of precisely diagnosing the cardiac function, intracardiac lead electrocardiography, and intrabronchial electrocardiography are well known.

As also known, in body-surface electrocardiography, electrocardiographic (ECG) lead electrodes are located at anatomically prescribed locations (usually, twelve regions) on the surface of the human body in order to detect an ECG lead current generated by the heart. This medical method is convenient because it can be easily effected by merely attaching the ECG lead electrodes to the surface of the human body. However, since the ECG lead electrodes are positioned at the locations far from the heart, the ECG lead current cannot sufficiently be detected. Particularly, this medical method is not applicable for searching for a location where there is a cardiac insufficiency.

The transesophageal lead electrocardiography is effected by inserting a catheter provided at its leading end portion with ECG lead electrodes into the esophagus through the oral cavity or nasal cavity and bringing the lead electrodes into contact with the internal surface of the esophagus so as to detect the ECG lead current. This medical method enjoys an advantage in that the lead electrodes can be positioned near the heart, especially, the posterior wall of the left atrium of the heart, thereby obtaining more reliable cardiac information compared with the aforenoted body-surface electrocardiography. However, this medical method demands skill in inserting the catheter into the esophagus and attaching the lead electrodes to the internal wall of the esophagus. Accordingly, this medical method cannot easily be practiced.

On the other hand, the intracardiac lead electrocardiography uses a catheter with ECG lead electrodes which is introduced into the heart through thick blood vessels and secured onto the internal wall of the heart in order to directly pick up a lead current. Thus, this is looked on as a medical method capable of obtaining the most precise cardiac information. However, this medical method entails a disadvantage in that it cannot easily be effected since it requires remarkably high-level surgical skill for inserting the catheter with the lead electrodes into the heart while X-ray the human body to secure the lead electrodes onto the anatomically prescribed locations in the heart with high accuracy.

In the intrabronchial electrocardiography similar to the transesophageal lead electrocardography, a catheter with ECG lead electrodes is inserted into the trachea or bronchus instead of the esophagus to detect the ECG lead current from the trachea or bronchus. This medical method is effected by positioning the ECG lead electrodes mounted on the leading end portion of the catheter at the bifurcation or the internal surface of at least one of the left and right bronchi in order to detect the ECG lead current near the heart. This intrabronchial electrocardiography also suffers a disadvantage in that, although an X-ray is conducted when inserting the lead electrodes into the trachea and bronchus, the lead electrodes disposed on the leading end portion of the catheter cannot easily be secured in position at the anatomically prescribed locations in the trachea or bronchus. The fact of the matter is that the catheter can be inserted into the trachea with relative ease because the trachea is hollow at all times, whereas the work of stably positioning the lead electrodes at the optimum locations in the trachea or bronchus often becomes much harder and more time-consuming, and moreover, possibly entails the risk of causing a patient pain. Under these circumstances, this medical method is scarcely available clinically.

As noted above, various medical methods for obtaining an electrocardiogram have been so far proposed and applied practically, but as is also apparent from the foregoing, body-surface electrocardiography makes it impossible to obtain precise cardiac information for diagnosing possible heart disorders, and transesophageal electrocardiography, intracardiac electrocardiography and intrabronchial electrocardiography disadvantageously call for high-level surgical skill and specific medical equipment and the task of inserting the lead electrodes which consumes much time and labor. However, a need has been earnestly felt for easy and reliable electrocardiography capable of obtaining precise cardiac information useful for making a diagnosis of heart disorders such as arrhythmia.

In light of the present circumstances, the inventors of this invention have studied intrabronchial electrocardiography and eventually developed new intrabronchial electrocardiography capable of being practiced easily and reliably.

As described above, conventional intrabronchial electrocardiography suffers from the defect that the lead electrodes cannot easily and stably be positioned at the anatomically prescribed locations in the trachea or bronchus. In particular, although the lead electrodes should be kept in close contact with the internal surface of the trachea or bronchus in order to obtain a precise electrocardiogram, the conventional intrabronchial electrocardiography has not employed means for stably retaining the lead electrodes at the suitable locations on the internal surface of the trachea or bronchus for effectively picking up the ECG lead current. Moreover, it is unacceptable to dislocate the lead electrodes in the trachea or bronchus, and thus, there has been a great need for a safe, reliable and handy intrabronchial catheter which can be suitably applied to intrabronchial electrocardiography and has ECG lead electrodes capable of being secured reliably at the anatomically prescribed locations in the trachea or bronchus.

SUMMARY OF THE INVENTION

An object of the present invention is to overcome the drawbacks of the conventional apparatus for obtaining a bronchial electrocardiogram by providing an apparatus capable of stably and reliably obtaining a bronchial electrocardiogram with a high accuracy, which has a structure capable of securely and easily retaining ECG lead electrodes at anatomically prescribed locations in the trachea or bronchus, and effectively detecting an ECG lead current.

Another object of this invention is to provide an apparatus for obtaining a bronchial electrocardiogram, which has a catheter capable of being safely and easily inserted into and pulled out from the trachea or bronchus without causing a patient pain.

A further object of this invention is to provide an apparatus for obtaining a bronchial electrocardiogram, which not only can conduct intrabronchial electrocardiography but also atrial pacing so as to obtain various cardiac information for diagnosing possible heart disorders such as supraventricular tachyarrhythmia and distinguishing supraventricular tachyarrhythmia from ventricular tachycardia while effecting the atrial pacing.

To attain the aforementioned objects according to this invention, there is provided an apparatus useful for obtaining a bronchial electrocardiogram, which comprises an elastic intrabronchial catheter to be inserted into the trachea or bronchus, at least one inflatable balloon disposed around the outer periphery at the leading end portion of the intrabronchial catheter, and one or more bronchial ECG lead electrodes mounted on the balloon.

An air tube is arranged along the intrabronchial catheter and has a leading end connected to the balloon and a tail end connected to an air pump so as to supply air to the balloon, thereby inflating the balloon. The bronchial ECG lead electrodes are connected to respective lead wires extending out of the intrabronchial catheter so as to be connectable to an electrocardiograph. When inserting the intrabronchial catheter into the trachea or bronchus, the balloon is first kept in its deflated state until the leading end of the intrabronchial catheter arrives at the trachea or bronchus. When the leading end of the catheter reaches a prescribed position in the trachea or bronchus, the balloon is inflated by being supplied with air through the air tube, thereby bringing the bronchial ECG lead electrodes in close contact with the internal wall of the trachea or bronchus to pick up effectively an ECG lead current for providing an electrocardiogram.

Other objects of this invention will become obvious upon an understanding of the embodiments about to be described and set forth in the appended claims, and various advantages not referred to herein will become apparent to those skilled in the art upon practicing the invention.

BRIEF DESCRIPTION OF THE DRAWINGS

Other objects and features of the present invention will be hereinafter explained in detail with reference to the accompanying drawings, wherein.

DESCRIPTION OF THE PREFERRED EMBODIMENTS

The present invention will become more fully understood from the detailed description given hereinbelow and the accompanying drawings which are given by way of illustration only, and thus are not limitative of the present invention.

Figure 1:
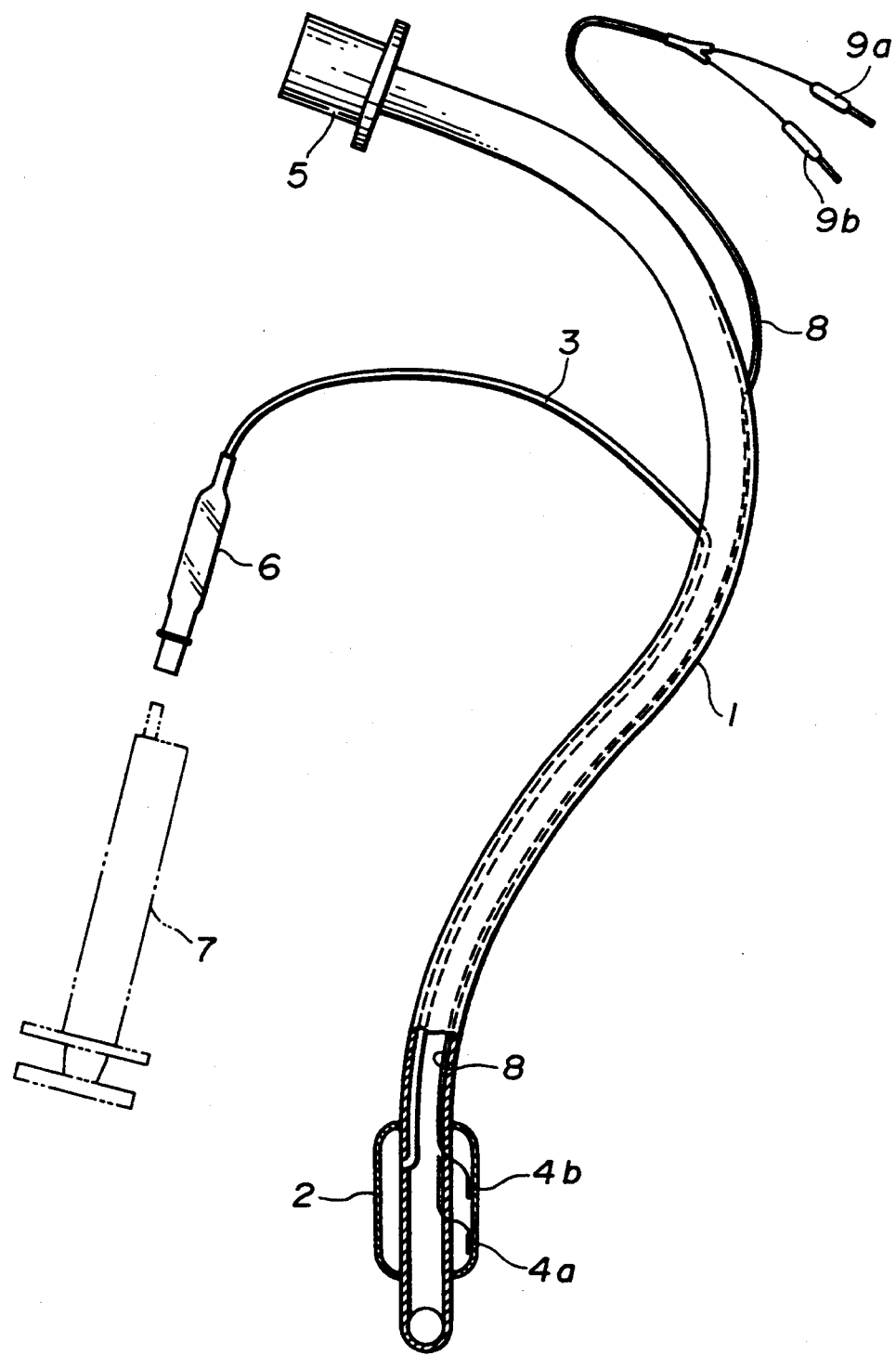
FIG. 1 is a partially sectioned side view showing one embodiment of a monitoring apparatus for use in obtaining a bronchial electrocardiogram according to this invention.
Figure 2:
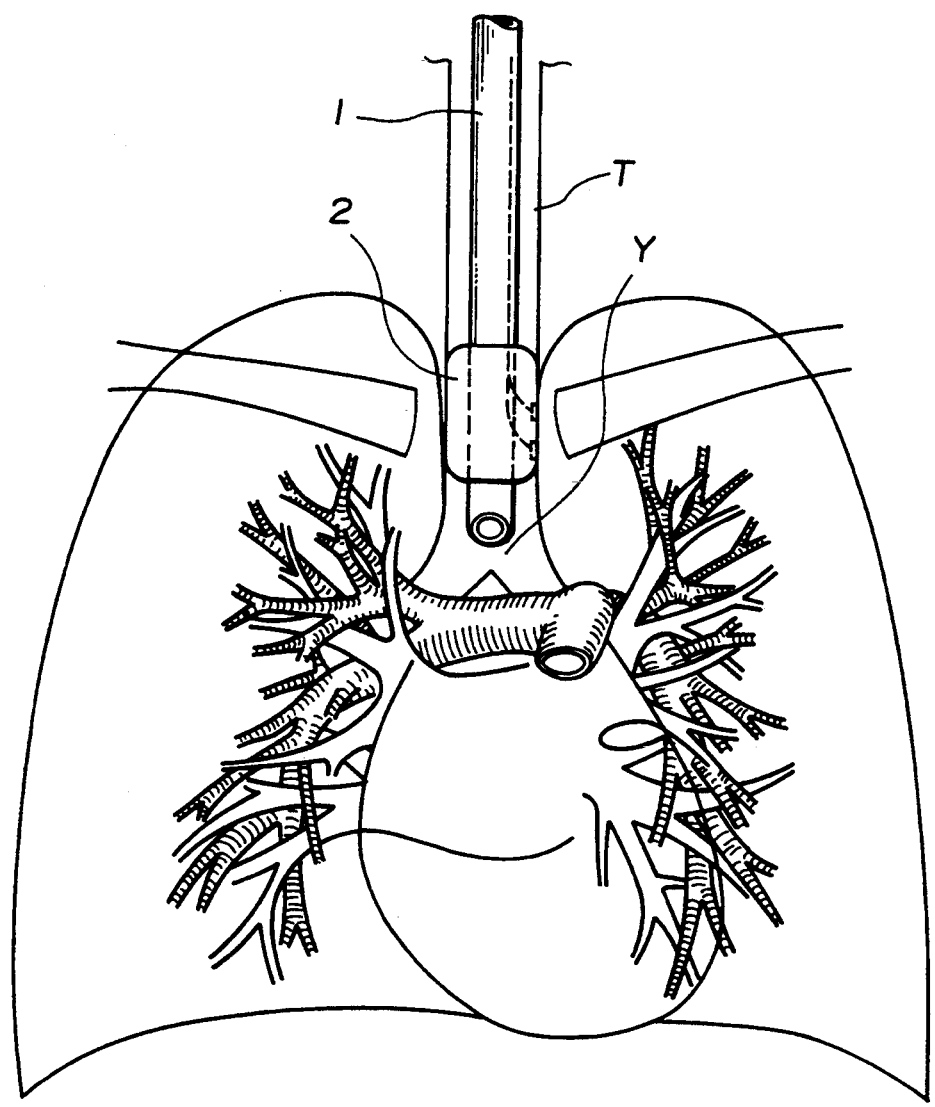
FIG. 2 is a schematic diagram of the apparatus in use.

The monitoring apparatus for use in obtaining a bronchial electrocardiogram according to this invention is shown in FIGS. 1 and 2 as one example and basically comprises an intrabronchial catheter 1 to be inserted into the trachea or bronchus, an inflatable balloon 2 disposed around the outer periphery of the leading end portion of the intrabronchial catheter 1, an air tube 3 for supplying air to the balloon 2, and bronchial ECG lead electrodes 4a and 4b mounted on the balloon 2.

The intrabronchial catheter 1 is made from an elastic material such as synthetic resins. In this embodiment, a tube to be inserted into the trachea T for the purpose of general anesthesia or artificial respiration may be used instead of a tube only useful as a catheter. In this case, the catheter 1 is provided at the tail end portion thereof with a connector 5 which is generally utilized to connect an air supply tube to an artificial respirator.

The balloon 2 mounted on the leading end portion of the catheter 1 is made of a thin membrane of synthetic resins or rubber, and has the shape of a bag enveloping the leading end portion of the catheter 1. The balloon 2 assumes a deflated state in its normal condition and is inflated by being supplied with air when the catheter 1 is completely inserted into the trachea as illustrated in FIG. 2.

The balloon 2 mounted on the catheter 1 has a function of not only fixedly retaining the leading end portion of the catheter 1 at a prescribed location in the trachea T, but also preventing the air introduced into the lungs through the outside periphery of the catheter 1 from leaking out. Therefore, the balloon 2 is designed so that the outer surface thereof comes into tight contact with the internal wall surface of the trachea or bronchus when supply of inflated with supply of air.

The air tube 3 enters inside the catheter 1 from the middle portion of the catheter and extends toward the leading end portion of the catheter along the internal surface of the catheter. Where the air tube 3 reaches the balloon 2, the air tube 3 pierces the wall of the catheter to be connected to the balloon. The air tube 3 is provided at the tail end thereof with a check valve 6 through which it is connected to an air pump 7 so as to supply the air to the balloon 2. Although the air pump 7 fundamentally serves to supply the air to the balloon 2, it may possess a function of releasing the air in the balloon 2 by force to deflate the balloon.

The bronchial ECG lead electrodes 4a and 4b are secured on the surface of the balloon 2 at a prescribed interval. The ECG lead electrodes are connected to respective lead wires 8 extending along the internal wall surface of the catheter 1 in the same manner as the air tube 3. The tail ends of the ECG lead electrodes have external terminals 9a and 9b connected to a not-shown electrocardiograph.

The locations at which the bronchial ECG lead electrodes 4a and 4b are attached to the balloon 2 are variously determined in accordance with the material of the balloon. In the case of using a balloon of non-conductive material such as rubber, the ECG lead electrodes may be attached to the outside of the membrane of the balloon. However, the ECG lead electrodes may be arbitrarily disposed on either side of the membrane of the balloon. In either case, the ECG lead electrodes must be secured so as not to fall away from the balloon when inserting the catheter into the trachea. Therefore, it is preferable to partially bury each electrode in the membrane of the balloon so as to expose a part of the electrode outside to ensure an electrical connection of the electrode to the internal wall surface of the trachea.

The aforementioned intrabronchial catheter 1 is applied practically in performing general anesthesia or inserted into the trachea T through the oral cavity or nasal cavity as illustrated in FIG. 2. The catheter 1 is introduced until the leading end thereof reaches the bifurcation of the trachea in the same way as a tube for general anesthesia. The bronchial ECG lead electrodes can easily be inserted into the trachea and located at the anatomically prescribed position on the bifurcation of the trachea by a person who has some experience of practicing medicine. When the leading end of the catheter reaches the anatomically prescribed location on the bifurcation of the trachea, air is supplied to the balloon 2 through the air tube 3 to inflate the balloon.

As mentioned above, the balloon 2 is inflated with air in the trachea, thereby bringing the outer surface of the balloon in tight contact with the internal wall surface of the trachea. Consequently, the ECG lead electrodes 4a and 4b are stably fixed in contact with the internal wall surface of the trachea, to thereby enable the ECG lead current to be detected through the lead wires 8.

When removing the catheter 1 from the trachea, the air in the balloon 2 is released through the air tube 3 by operating the air pump, thereby deflating the balloon.

In the illustrated embodiment, the catheter 1 has the connector 5 at the tail end thereof because the catheter is in the form of a common tube for use in general anesthesia or artificial respiration but the connector 5 is by no means necessary to this invention.

Furthermore, the balloon 2 may be provided with only a single bronchial ECG lead electrode or a plurality of ECG lead electrodes. When using a single bronchial ECG lead electrode, a counterpart ECG lead electrode may be attached onto the surface of the human body. When using a plurality of ECG lead electrodes, the electrodes are arranged on the membrane of the balloon at intervals. Also, when using the plurality of ECG lead electrodes, the electrodes must fundamentally be disposed in pairs, but the number of the electrodes should not be understood as limitative.

Figure 3:
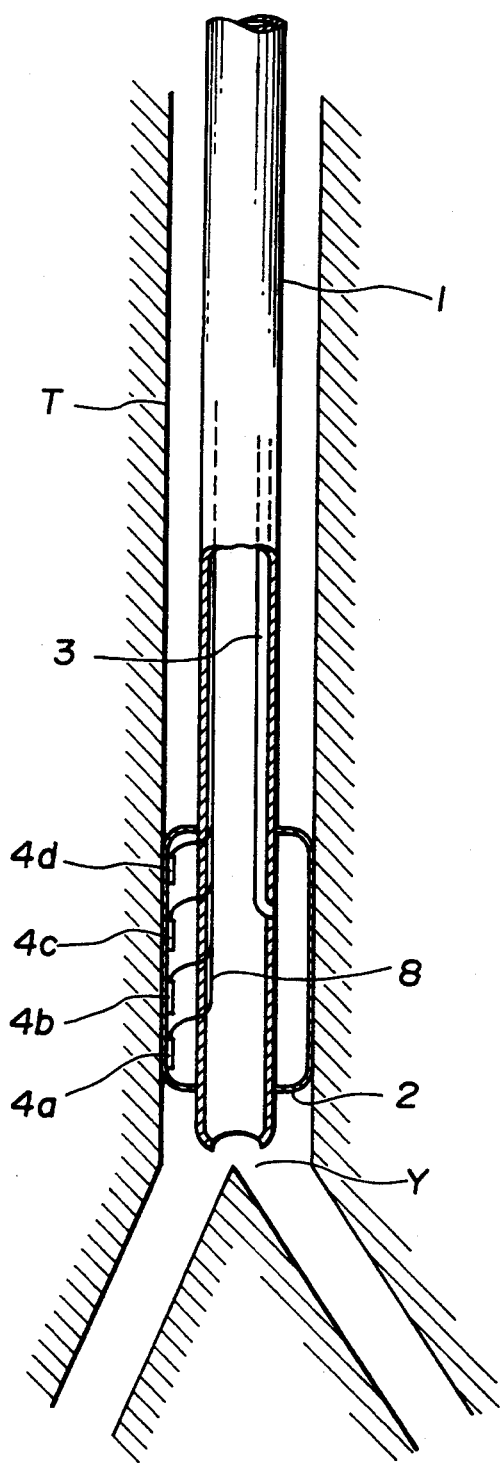
FIG. 3 is an enlarged view showing another embodiment having four ECG lead electrodes mounted in line on one peripheral side of a balloon.
Figure 4:
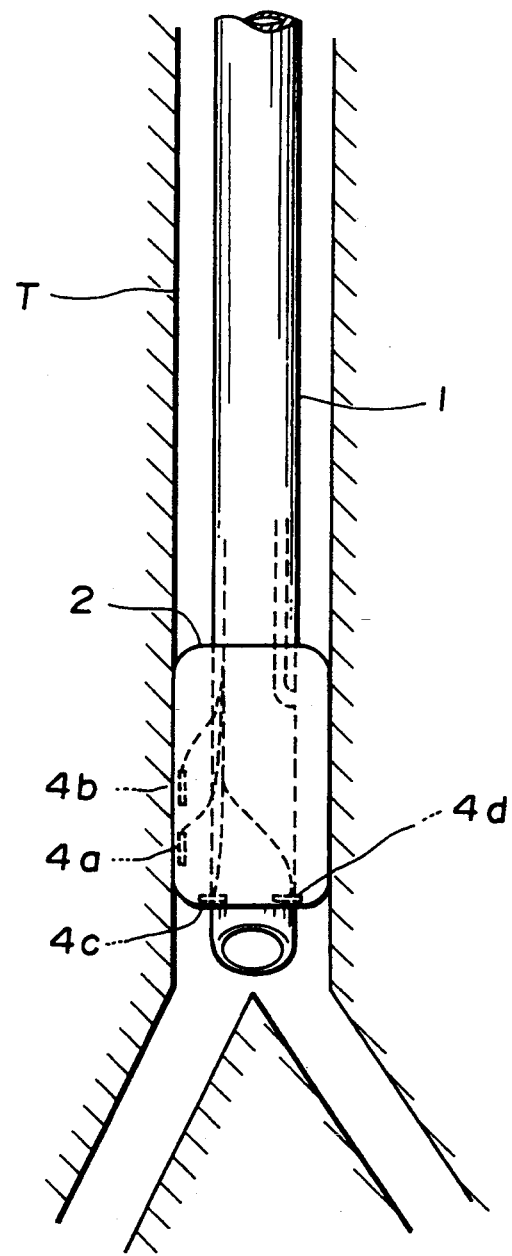
FIG. 4 is an enlarged view showing still another embodiment having two ECG lead electrodes mounted on one peripheral side of a balloon.
Figure 5:
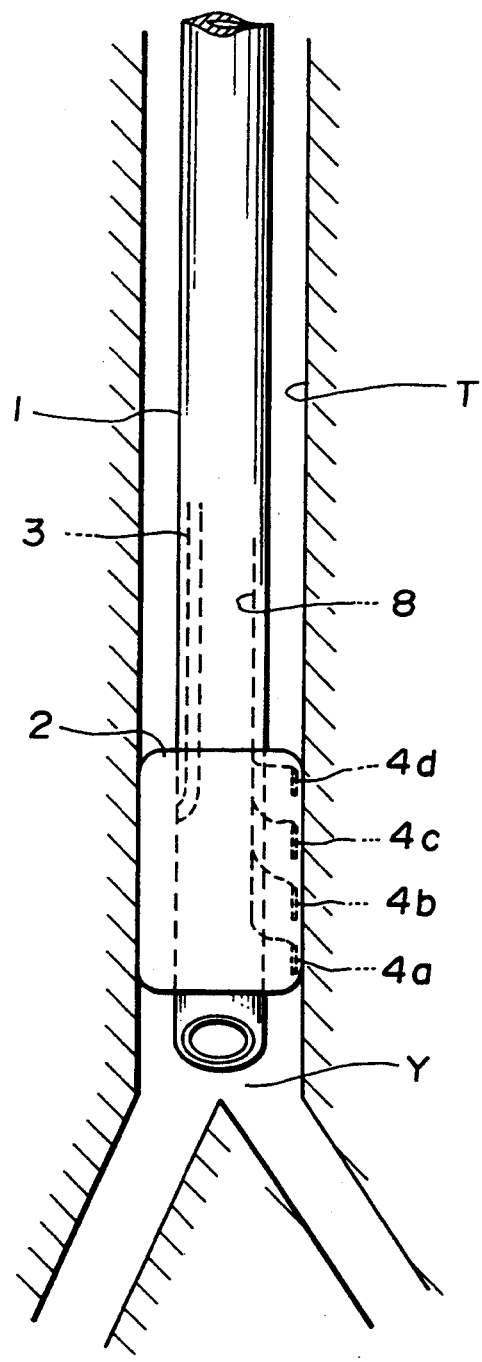
FIG. 5 is an enlarged view showing yet another embodiment having four ECG lead electrodes mounted on the other peripheral side of a balloon.

FIG. 3 through FIG. 5 illustrate other embodiments of modified catheters each having additional bronchial ECG lead electrodes 4c and 4d on the balloon 2. These catheters can be applied for not only monitoring the heart to obtain a bronchial electrocardiogram but also for effecting cardiac pacing.

In the embodiment shown in FIG. 3, four bronchial ECG lead electrodes 4a, 4b, 4c and 4d are arranged on the left side portion of the membrane of the balloon 2 in line in the lengthwise direction of the catheter. It is possible to use the pair of ECG lead electrodes 4a and 4c as monitoring electrodes for obtaining an electrocardiogram, and the pair of ECG lead electrodes 4b and 4d for effecting cardiac pacing. The ECG lead electrodes of the pairs are arranged alternately in line at regular intervals so as to ensure a sufficient distance between the paired electrodes for effectively detecting the ECG lead current. Thus, when practicing cardiac pacing, the ECG lead electrodes sufficiently separated can be applied to detect a faint pacing current, and therefore, a patient will hardly feel an unpleasant sensation such as that which the patient would feel if cauterizing occurred. The ECG lead electrodes arranged in line in this embodiment are separated by a distance of about 20 mm so as to leave a distance of 40 mm between the electrodes 4a–4c and 4b–4d which are substantially paired off.

In the embodiment shown in FIG. 4, two bronchial ECG lead electrodes 4a and 4b are attached to the peripheral side surface of the balloon 2, and another set of two bronchial ECG lead electrodes 4c and 4d are attached to the front surface of the balloon. The embodiment shown in FIG. 5 has four bronchial ECG lead electrodes 4a, 4b, 4c and 4d arranged in line on the right side surface of the balloon 2.

These embodiments having the different arrangements of the ECG lead electrodes are expected to provide different on the other hand, when the inventors experimentally produced some intrabronchial catheters based on these embodiments and effected the cardiac pacing, differences in their performance were not noticeable even from careful observation.

As was touched on earlier, the bronchial ECG lead electrodes can easily be inserted into the trachea and located at the anatomically prescribed position on the bifurcation of the trachea by a person skilled in practicing medicine. However, even the inflated balloon 2 slightly deviates from the prescribed position on the bifurcation, whereby the ECG lead electrodes are displaced from the anatomically prescribed locations in the trachea or bronchus, the electrocardiogram is not affected too much.

Figure 6:
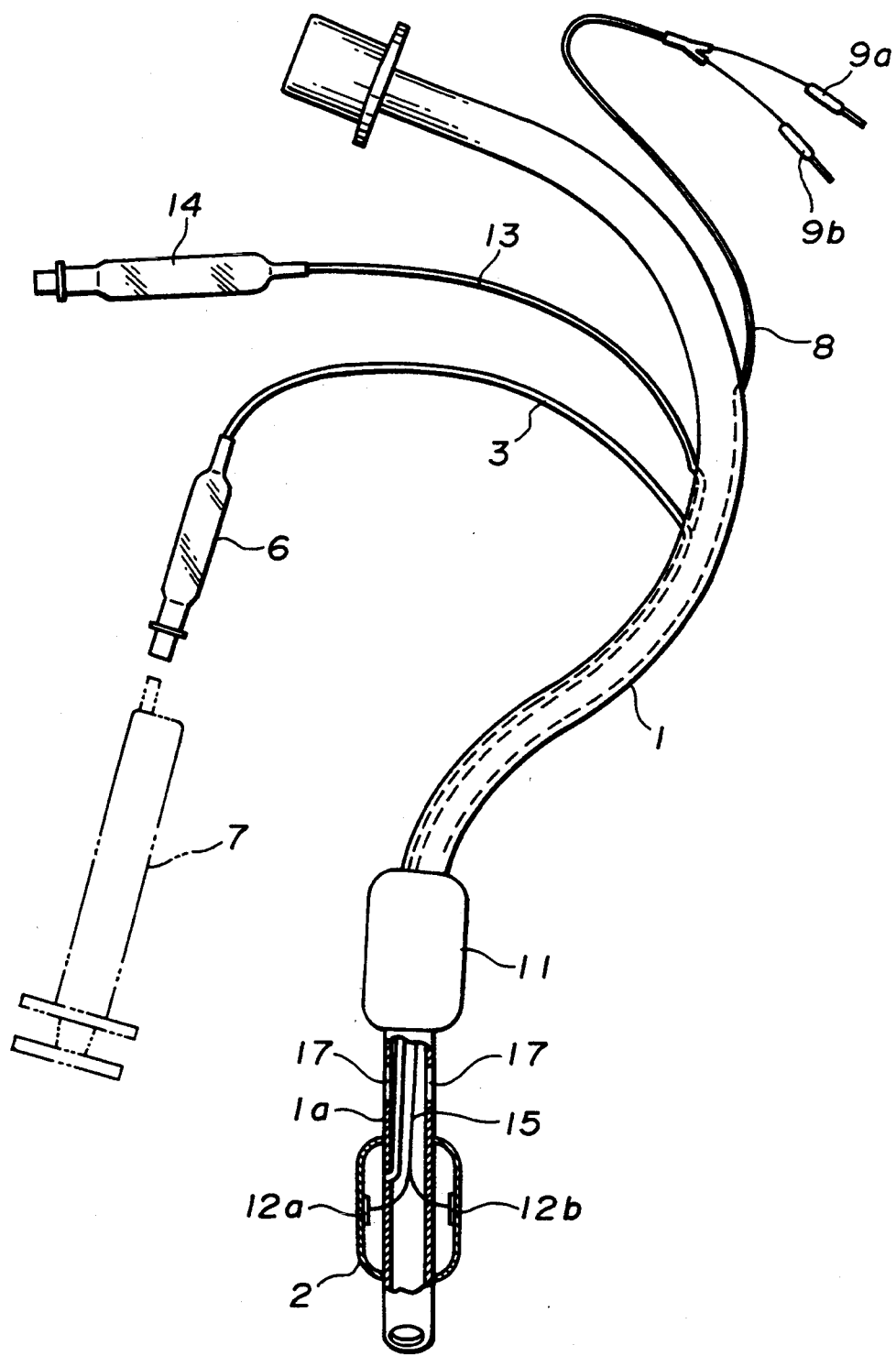
FIG. 6 is a partially sectioned side view showing a further embodiment of an apparatus according to this invention, having an auxiliary balloon.
Figure 7:
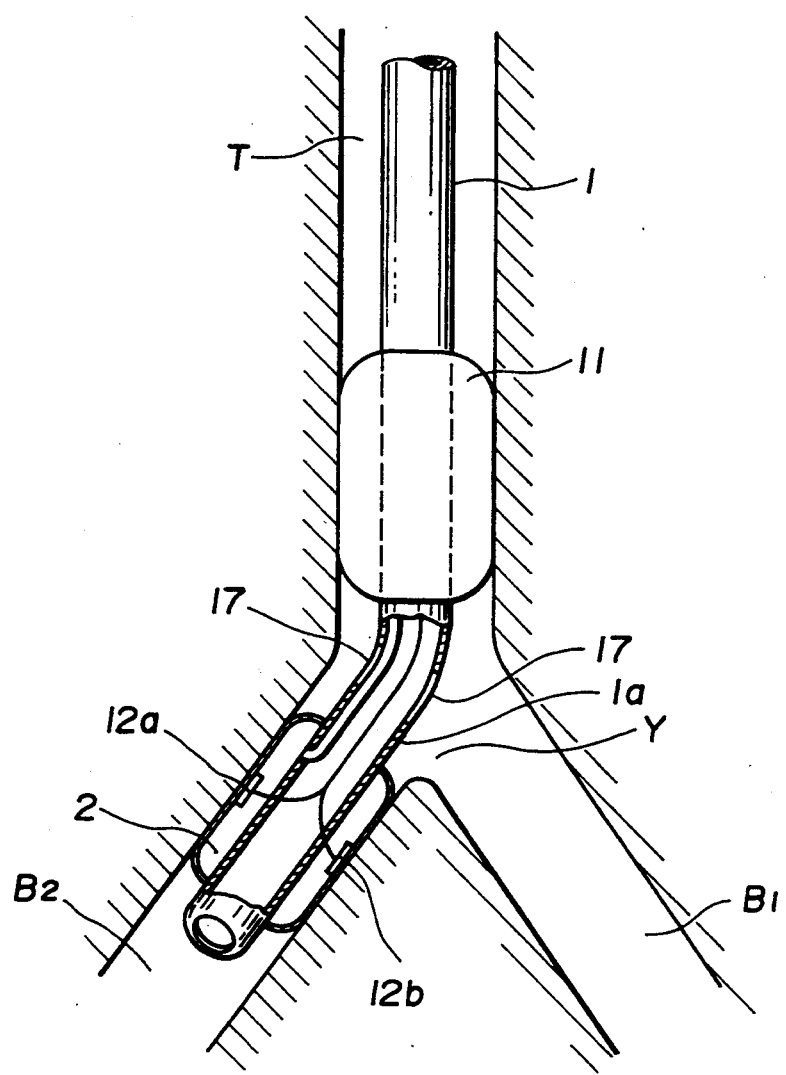
FIG. 7 is an enlarged view showing principal portion of the apparatus shown in FIG. 6.

Next, a modified embodiment of the apparatus for monitoring the heat to obtain bronchial electrocardiogram according to this invention will be described with reference to FIG. 6 and FIG. 7. The apparatus in this embodiment has an auxiliary balloon 11 for supporting the intrabronchial catheter 1 in addition to the balloon 2 with the ECG lead electrodes 12a and 12b. The auxiliary balloon 11 is disposed at a location distant from the primary balloon 2 at the leading end portion of the catheter 1 by a suitable distance.

The auxiliary balloon 11 is connected to an air tube 13 which extends along the internal surface of the catheter 1 in the same manner as the air tube 3 connected to the primary balloon 2. Similarly to the air tube 3 with the check valve 6, the air tube 13 is also provided at the tail end thereof with a check valve 14 through which the air tube 13 is connected to an air pump. By selectively operating the air pumps, the balloons 2 and 11 can be optionally inflated or deflated.

The ECG lead electrodes 12a and 12b in this embodiment are connected to external terminals 9a and 9b through lead wires 8 extending along the internal surface of the catheter 1.

The ECG lead electrodes 12a and 12b are disposed one on either side of the outer surface of the balloon 2, and can be used as electrodes for obtaining an electrocardiogram or for effecting cardiac pacing.

In the illustrated embodiment, reference numeral 17 denotes vent holes formed in the leading end portion 1a of the catheter 1 between the balloons 2 and 11.

The intrabronchial catheter 1 in this embodiment is inserted into the trachea until the balloon 2 reaches the bifurcation of the trachea, and thereafter, both the balloons 2 and 11 are inflated by being supplied with air through the respective air tubes. The balloon 2 may be inserted into the right or left bronchus B1 or B2. In FIG. 7, the balloon 2 is inserted into the left bronchus B2 and inflated with air, thereby bringing the ECG lead electrodes 12a and 12b into close contact with the internal wall surface of the bronchus.

The vent holes 17 serve as paths for permitting air to flow into the right bronchus B1.

The intrabronchial catheter 1 in this embodiment is inserted across the bifurcation of the bronchus B2 so that the ECG lead electrodes 12a and 12b can be brought closer to the heart. Therefore, precise cardiac measurement or cardiac pacing can be effected with ease.

To facilitate the insertion of the intrabronchial catheter into the trachea and further into the bronchus having a smaller inner diameter than the trachea, it is desirable to make the balloon 2 smaller in diameter when inflated than the inflated balloon 11, and the part 1a of the intrabronchial catheter between the balloons 2 and 11 may preferably be made rather small in diameter.

As is described above, although the apparatus according to this invention was fundamentally developed for the purpose of obtaining a bronchial electrocardiogram for diagnosing the cardiac function, this apparatus can be effectively applied to transbronchial atrial pacing which is effected by inserting the intrabronchial catheter into the bronchus near the atrium of the heart in the manner identical to transesophageal atrial pacing which is effected by inserting pacing electrodes into the esophagus. When practicing the transbronchial atrial pacing by using the apparatus according to this invention, the connection of the bronchial ECG lead electrodes mounted on the balloon in this invention may be switched from an electrocardiograph to a pacing device for imparting electrical stimulation to the heart. However, since the atrial pacing which is generally effected while monitoring the cardiac function requires plural sets of the bronchial ECG lead electrodes, at least four ECG lead electrodes are necessary. Also, the ECG lead electrodes are required to be arranged at regular intervals as described above. In this respect, the apparatus of this invention has a simple structure facilitating the arranging of the ECG lead electrodes at regular intervals on the surface of the balloon with cardiac pacing, differences in their performance; whereby the bronchial ECG lead electrodes can be readily positioned at anatomically prescribed locations on the internal surface of the trachea or bronchus.

As is apparent from the detailed description above, according to this invention, by inserting the intrabronchial catheter into the trachea or bronchus and supplying air to the balloon through the air tube to inflate the balloon in the trachea or bronchus, the bronchial ECG lead electrodes can easily be secured stably in close contact with the internal wall surface of the trachea or bronchus. Moreover, by releasing the air from the inflated balloon, the ECG lead electrodes can safely be pulled out from the trachea or bronchus with ease. Thus, the intrabronchial catheter of this invention can be easily inserted into the trachea or bronchus and the bronchial ECG lead electrodes can be reliably positioned at anatomically prescribed locations in the trachea or bronchus near the heart, and therefore proves advantageous in obtaining a bronchial electrocardiogram. Since the bronchial ECG lead electrodes can be secured close to an atrium of the heart, the apparatus of this invention can be efficiently used for not only detecting an ECG lead current for providing an electrocardiogram, but also for effecting atrial pacing.

Furthermore, since the intrabronchial catheter of this invention can be tube for general anesthesia or artificial respiration, it is convenient from the standpoint of medical treatment because general anesthesia or artificial respiration can be easily conducted while obtaining a electrocardiogram.

As described above, since the apparatus for obtaining a bronchial electrocardiogram according to this invention can not only be used for intrabronchial electrocardiography but also for atrial pacing, various cardiac information for diagnosing possible heart disorders such as supraventricular tachyarrhythmia and distinguishing supraventricular tachyarrhythmia from ventricular tachycardia can be reliably obtained with ease.

It is to be understood that the invention is not limited to the details and arrangement of its parts illustrated in the accompanying drawings, since the invention is capable of other embodiments and of being practiced or carried out in various ways. Also, it is to be understood that the phraseology or terminology employed herein is for the purpose of description and not of limitation.

What is claimed is:

1. Apparatus for obtaining a bronchial electrocardiogram and effecting cardiac pacing, said apparatus comprising:
   an elastic hollow intrabronchial catheter capable of being inserted into the trachea or bronchus, said catheter having a leading end portion,
   an electrically non-conductive inflatable balloon disposed at the leading end portion of said intrabronchial catheter;
   two pairs of bronchial ECG electrodes which detect an ECG lead current and effect cardiac pacing, respectively,
   two of said bronchial ECG lead electrodes being mounted on an inflatable portion of said balloon so as to move outwardly away from said catheter as the balloon is being inflated;
   the others of said bronchial ECG lead electrodes also being mounted to said balloon;
   an air tube extending along said catheter and having a leading end connected to said balloon such that air can be introduced into said balloon from said tube; and
   said balloon being inflatable to a degree at which said balloon can contact an inner wall portion of the trachea or bronchus such that said ECG electrodes can be brought to anatomically prescribed locations on the inner wall portion when the catheter is inserted into the trachea or bronchus and the balloon is inflated to said degree.

2. The apparatus according to claim 1 wherein said bronchial ECG lead electrodes are arranged at prescribed intervals.

3. The apparatus according to claim 1, and further comprising an air pump connected to said balloon via said air tube, the pump supplying the air to inflate said balloon.

4. The apparatus according to claim 1, and further comprising an air pump and a check valve connected to said balloon via said air tube, said pump supplying the air to inflate said balloon.

5. The apparatus according to claim 1, wherein said intrabronchial catheter has a connector connectable to an air supply tube of an artificial respirator so that a patient can breath using an artificial respirator as the catheter is inserted into the trachea or bronchus and when the balloon is inflated in the trachea or bronchus.

6. The apparatus according to claim 1, and further comprising lead wires which extend along an internal wall surface of said catheter, and external terminals of an electrocardiograph, said lead wires being connected to said ECG lead electrodes which detect an ECG current and to said external terminals.

7. The apparatus according to claim 1, wherein said ECG lead electrodes are arranged in line at regular intervals.

8. The apparatus according to claim 7, wherein the ECG lead electrodes which detect an ECG lead current are alternately disposed with the ECG lead electrodes which effect cardiac pacing.

9. The apparatus according to claim 1, wherein said balloon has a side peripheral surface on which said two of the bronchial ECG lead electrodes are mounted and a front surface on which the others of said ECG lead electrodes are mounted.

10. The apparatus according to claim 9, wherein the ECG electrodes which detect an ECG lead current are mounted on said side peripheral surface and said front peripheral surface, respectively, and the ECG lead electrodes which effect cardiac pacing are mounted on said side peripheral surface and said front peripheral surface, respectively.

11. The apparatus according to claim 1 further comprising an auxiliary balloon disposed on said intrabronchial catheter distant from said balloon.

12. The apparatus according to claim 11, wherein said intrabronchial catheter has at least one vent hole extending therethrough at a location between said balloons.

* * * * *